US009730502B2

(12) United States Patent
Naura (10) Patent No.: US 9,730,502 B2
(45) Date of Patent: Aug. 15, 2017

(54) SUBSTANCE APPLICATOR (71) Applicant: Eman Naura, Dearborn Heights, MI (US)

(72) Inventor: Eman Naura, Dearborn Heights, MI (US)

( * ) Notice: Subject to any disclaimer, the term of this patent is extended or adjusted under 35 U.S.C. 154(b) by 0 days.

(21) Appl. No.: 14/808,181

(22) Filed: Jul. 24, 2015

(65) Prior Publication Data
US 2016/0022013 A1 Jan. 28, 2016

Related U.S. Application Data (60) Provisional application No. 62/028,605, filed on Jul. 24, 2014.

(51) Int. Cl.
| A45D 40/26 | (2006.01) |
| A61M 35/00 | (2006.01) |
| B05B 11/00 | (2006.01) |
| A45D 34/04 | (2006.01) |
| A45D 34/06 | (2006.01) |
| A45D 40/18 | (2006.01) |

(52) U.S. Cl.
CPC ......... *A45D 40/265* (2013.01); *A61M 35/003* (2013.01); *B05B 11/0089* (2013.01); *A45D 34/04* (2013.01); *A45D 34/045* (2013.01); *A45D 34/06* (2013.01); *A45D 40/18* (2013.01); *A45D 2200/056* (2013.01); *A45D 2200/1081* (2013.01); *B05B 11/30* (2013.01)

(58) Field of Classification Search
CPC .............. A45D 43/265; A45D 2200/10; A45D 2200/1081; A46B 9/021; A46B 9/005; A47K 7/028; A61M 35/003; B05B 11/0089
See application file for complete search history.

(56) References Cited

U.S. PATENT DOCUMENTS

| 1,962,875 | A | 6/1934 | Reber |
| 2,034,416 | A | 3/1936 | Peat |
| 6,196,743 | B1 | 3/2001 | Brucker |
| 6,325,561 | B1 | 12/2001 | Reynolds |
| 6,357,945 | B1 | 3/2002 | Losier et al. |
| 6,533,144 | B2 | 3/2003 | Davies et al. |
| 6,835,019 | B2 | 12/2004 | White |
| 6,986,617 | B1 | 1/2006 | Denker |
| 7,537,140 | B2 | 5/2009 | Lin |
| 8,844,776 | B2 | 9/2014 | Haas et al. |
| 8,961,050 | B2 * | 2/2015 | Chesson ............... A45D 34/045 401/118 |
| 2003/0108846 | A1 * | 6/2003 | Hoertsch ................ A46B 9/005 433/216 |
| 2004/0018037 | A1 | 1/2004 | Gueret |

* cited by examiner

*Primary Examiner* — Jennifer C Chiang
*Assistant Examiner* — Bradley Oliver
(74) *Attorney, Agent, or Firm* — Young Basile (57) ABSTRACT

An applicator device that includes a tube member having an elongated body with outer surface, a first end and an opposed second end and an applicator member attached to a portion of the outer surface of the elongated body of the tube member and extending around the circumference of the tube member, the applicator member including a plurality of flexible frustoconical tendrils projecting outward from the outer surface of the elongated member.

19 Claims, 6 Drawing Sheets

SUBSTANCE APPLICATOR

CROSS-REFERENCE TO RELATED APPLICATIONS

This application claims priority to U.S. Provisional Patent Application No. 62/028,605 filed Jul. 24, 2015, which is hereby incorporated by reference in its entirety.

BACKGROUND

The present invention relates to devices for applying items such as, but not limited to, sun tan lotions, creams, body lotions, body oils, ointments, soaps, etc. (aforementioned to be referred to as "substances" throughout this patent) on ones back and other difficult to reach areas of the body without having to secure items additional to the substances' containers and/or parts.

It is difficult for most people to apply substances to one's own back and, in some cases, other parts of the body. Therefore many individuals either skip adding lotion to this portion of the body, are forced to have someone apply the substance for them, or purchase additional items/applicators to apply said substances.

Most current applicators are bulky, larger than necessary, difficult to store, and a costly addition to a person's toiletries. The applicator at hand can addresses all of the above problems.

In addition, current applicators are often not able to be cleaned so they become a health hazard. This applicator will drastically surpass other applicators because of its convenience, instant availability, ease of storage, ease of use, cost, and functionality.

Thus, it would be desirable to provide a method and device which addresses such challenges.

SUMMARY

An applicator device that includes a tube member having an elongated body with outer surface, a first end and an opposed second end and an applicator member attached to a portion of the outer surface of the elongated body of the tube member and extending around the circumference of the tube member, the applicator member including a plurality of flexible frustoconical tendrils projecting outward from the outer surface of the elongated member

BRIEF DESCRIPTION OF THE DRAWING

In order to further illustrate and describe the invention disclosed, attention is directed to the various drawing figures in which like reference numerals are employed for like elements throughout the various views and figures.

DETAILED DESCRIPTION

Disclosed herein is a applicator that can be employed to deposit various substances on various regions of the body; particularly regions that are difficult of an individual to reach including but not limited to the back, extremities and the like. The applicator can be used to apply lotions, creams, oils, gels, soaps, ointments, medications and other liquid substances (hereby known as topical substances) to areas of the body. The applicator may be attached to the existing tube, cylindrical object or elongated rod, or other object and used in conjunction with bottles of topical substances. The lid/cap/pump of the bottle can be loosened and the tube with attached applicator attached to it can be pulled out of the container.

The applicator can be used to apply the topical substance on all areas of the human, or animals, body and then placed back in the container and sealed so that the container used as pump applicator or capped as desired. It is contemplated that the applicator as disclosed herein can add functionality of the container whether it be a pump, cap, or basic lid, or squirt lid.

As broadly disclosed herein, the applicator can be made of a material that is, plastic, sponge, rubber, foam, microfiber, extended foam core and/or other material(s) so that it may be coated with substances. In certain embodiments, the applicator can be made of a material or materials that will confine the topical substance to it during removal from an associated container and allow for the topical substances to be easily, evenly, and effectively spread along the surface of the body in areas the user(s) chose. Some of the application areas will be areas that users cannot typically reach without assistance. These typically include backs and the like. It is also understood that the applicator device as disclosed herein can also be successfully used by individuals with physical impairments and/or challenges to apply topical substances to difficult-to-reach areas of the body that can include feet, legs, arms and the like. The apparatus as presently disclosed will permit individuals be able to reach parts of their body with only the assistance of the applicator and apply the contents of an associated container containing the topical substance desired.

Figure 1:
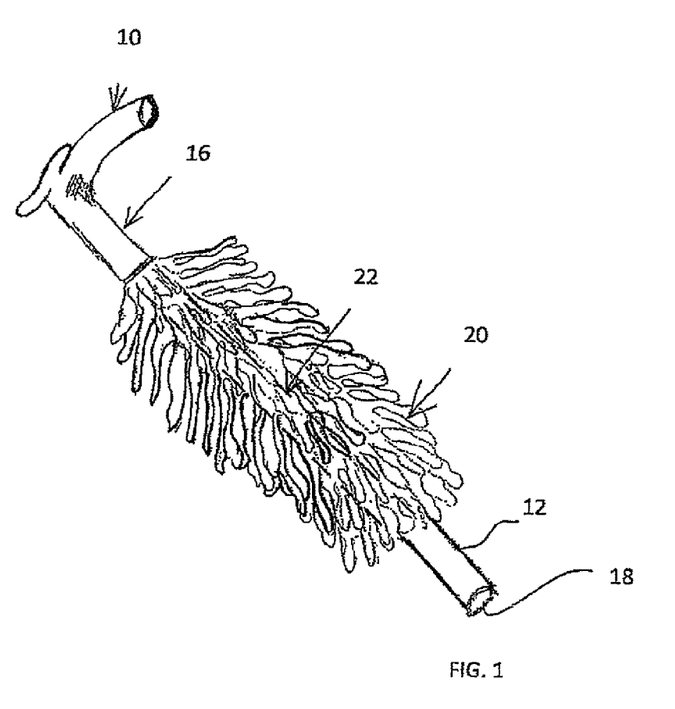
FIG. 1 is a perspective view of a first embodiment an applicator as disclosed herein.

As illustrated in FIG. 1, the applicator device 10 may include a topical substance-conveying tube 12 in fluid communication with a pump mechanism 14 having a pump device 16 having outlet 17 such that material substance drawn into the tube end 18 distal to the pump mechanism 14.

Figure 6:
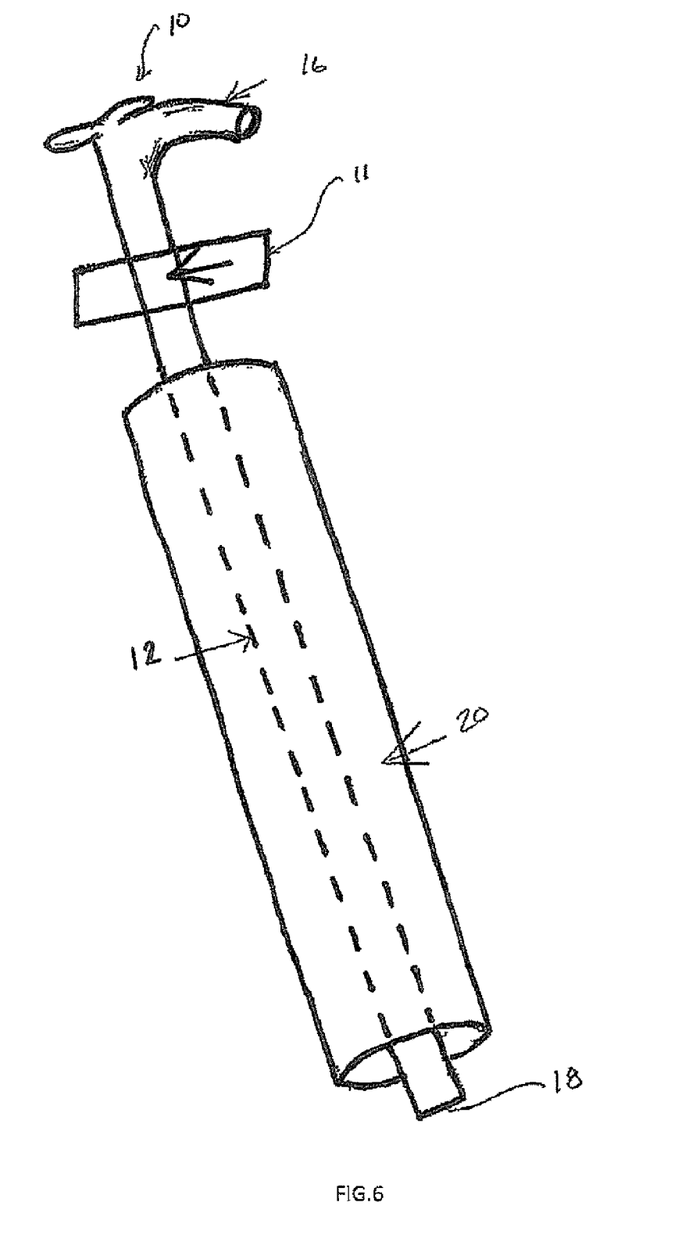
FIG. 6 is a perspective view of a third alternate embodiment of an applicator as disclosed herein.
Figure 7:
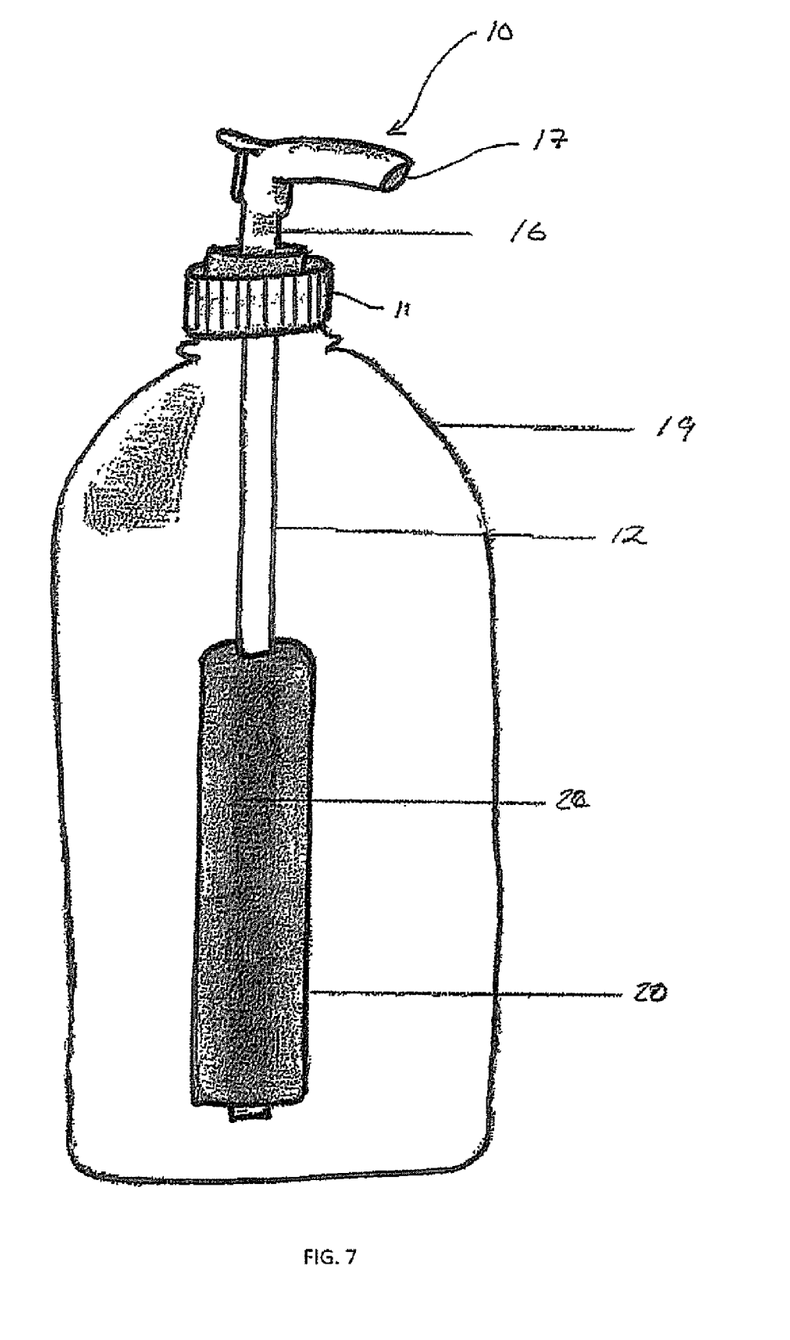
FIG. 7 is a side view of the container device employing the third alternate embodiment of the applicator device as disclosed herein.
Figure 8:
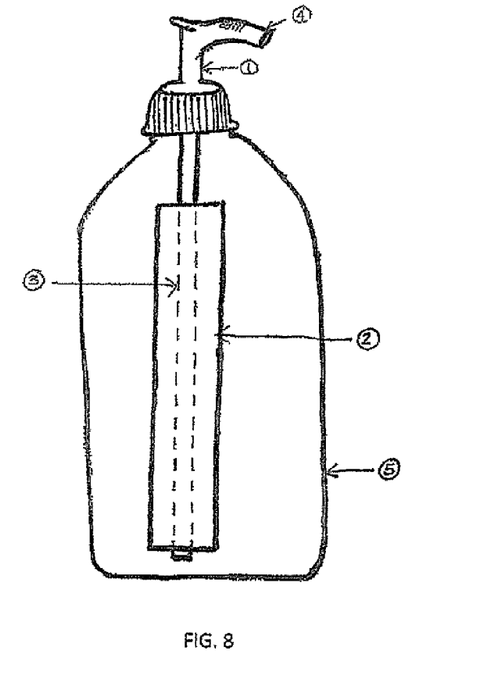
FIG. 8 is an interior view of the container device of FIG. 7.

The applicator device 10 can be configured to be associated with a suitable cap 1, if desired or required, as would be employed if the applicator device 10 is to be used with a bottle or other container. One non-limiting example of an applicator device 10 includes a cap 11 is illustrated in FIG. 6. The cap 11 can have a suitable attachment mechanism to secure the applicator device 10 to an associated container 19 as is illustrated in FIG. 7. In certain embodiments, the cap 11 may have a screw-on configuration. In other configurations, the cap 11 may have a suitable pinch release mechanism as desired or required.

The substance conveying tube 12 is embedded in an applicator member 20. As depicted in FIGS. 1-5 the applicator member 20 is composed of a plurality of individual tendrils 22 that extend from a connection location that proximate to the topical substance conveying tube 12 to a location distal thereto.

The individual tendrils 22 can have a configuration suitable to pick up a volume of topical substance from the associated container and transfer it to body part to which it is to be applied. In certain embodiments, the tendrils are positioned and configured such that a measured amount of material to be applied. The individual tendrils 22 can be made of a flexible polymeric material such as rubber, silicone, etc.

Figure 2:
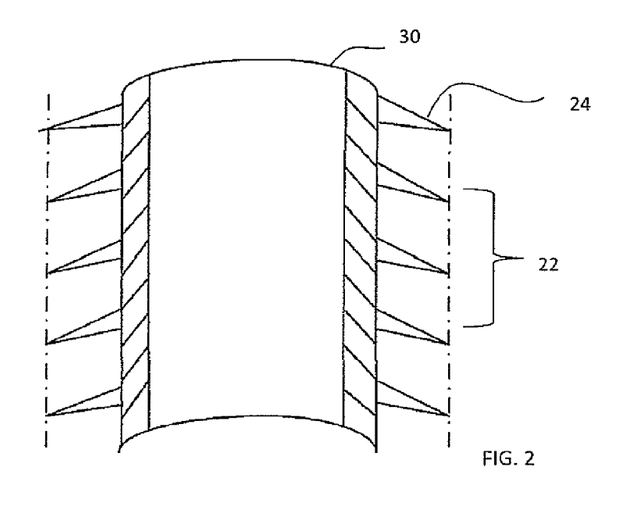
FIG. 2 is a cross-sectional view of a detail of an embodiment of tendrils that can be employed in the applicator as disclosed herein and mounted to a sheath member.

The tendrils 22 can be positioned at a concentration between 5 and 30 tendrils per square inch in certain embodiments. While the tendrils 22 can have any configuration, in certain embodiments, the tendrils can have a configuration similar to that depicted in FIGS. 2-3 and 5. As illustrated in FIG. 2, the individual tendrils 22 can be configured as frustoconical members 24 having a tapered body 26 and a generally rounded end surface 28. It is contemplated that the frustoconical tendrils may have a maximum cross-sectional diameter proximate to the topical substance conveying tube 12 that is between 1/8 and 1/4 inch tapering to a cross-sectional diameter between 1/8 and 1/32 of an inch proximate to the rounded end surface 28. The frustoconical tendrils 22 used in the applicator member 20 can have individual lengths between 1/2 inch and 3 inches, with individual lengths between 1/2 and 1.5 inches being employed in some embodiments. It is contemplated that the tendrils 22 in the applicator member 20 can be a mixture of lengths to produce an average tendril length between 3/4 inches and 1 inch in certain embodiments.

The individual tendrils 22 can be positioned in staggered, spaced relationship to one another and may be oriented at an angle relative to substance conveying tube 12 that is between about 20 degrees to about 90 degrees such that the tips or end surfaces 28 are oriented toward the tube end 18 distal to the pump mechanism 14, cap 11 or the like. The tendrils 22 have sufficient flexibility to splay and flex when inserted into a container of topical substance to be applied and to retain a sufficient quantity of the topical substance on and in between the individual tendrils 22 during removal from the associated container.

Figure 3:
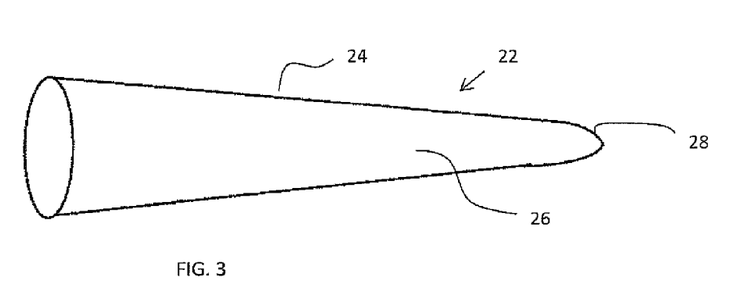
FIG. 3 is a detail view of an embodiment of one tendril configuration that can be used in the applicator as disclosed herein.
Figure 4:
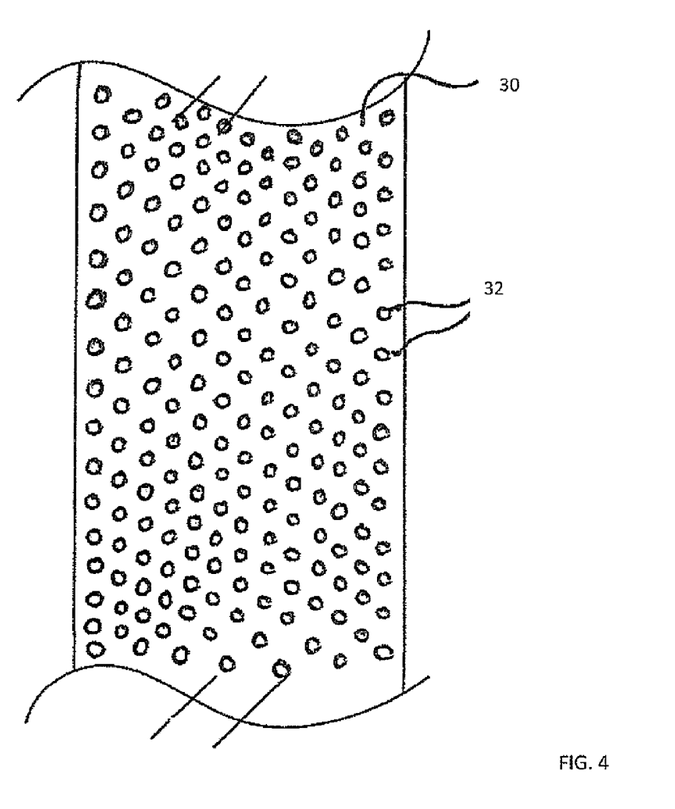
FIG. 4 is a detail view of one embodiment a tendril mounting pattern for use with the applicator as disclosed herein.
Figure 5:
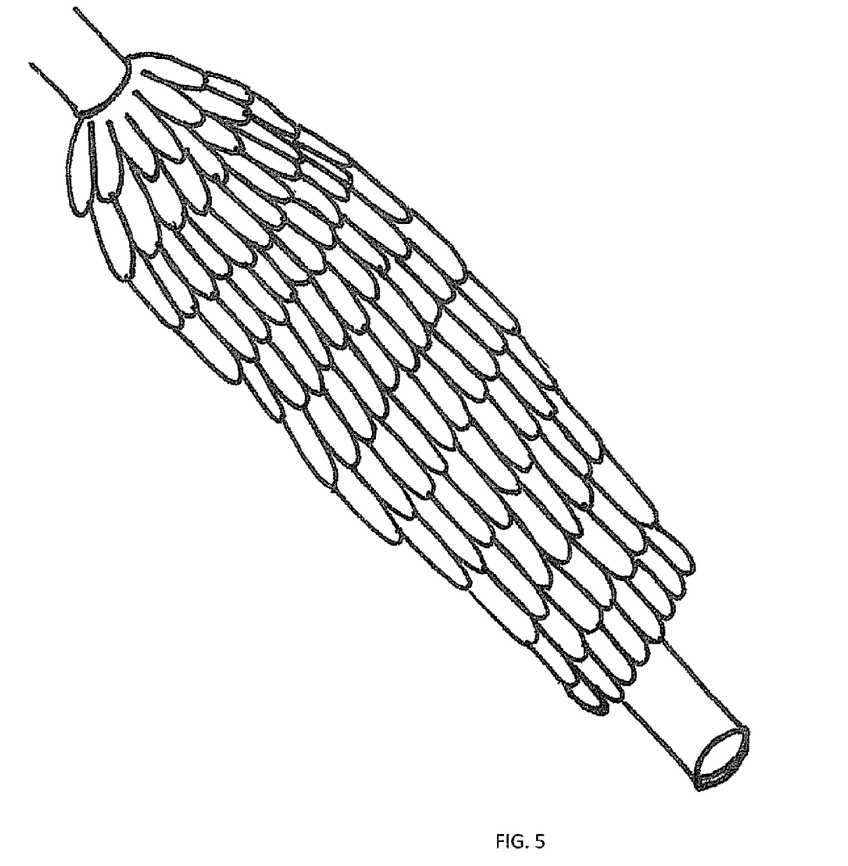
FIG. 5 is a perspective view of a second embodiment of an applicator as disclosed herein.

In the tendril embodiment depicted in FIGS. 2 and 3, it is believed that the frustoconical configuration facilitates efficient transfer of material from the associated container and carrying the material to the desired body location. The material can be transferred from contact with the tendrils 22 to the skin of the user by a suitable sliding and pressing motion. Where some or all of the individual tendrils 22 are configured as frustoconical members 24, it is believed that the contact action will stimulate the skin as the topical substance is applied. It is also believed that the movement of the various frustoconical members 24 either relative to one another or relative to tendrils 22 of other configurations causes a scraping motion that urges the transferred topical substance off the frustoconical members 24 as well as other tendrils 22 and on to the skin of the user.

The individual tendrils 22 can be positioned relative to the topical substance conveying tube 12 in either a random or geometric pattern and can be connected to the material conveying tube 12 in any suitable manner. One non-limiting example of such a pattern includes that spiral pattern as shown in the embodiment depicted in FIG. 4. Other patterns include those illustrated in FIGS. 1 and 5. In certain embodiments where frustoconical members 24 are employed either also or in combination with tendrils 22 having other configurations, the frustoconical members 24 can be configured in a spiral pattern. Without being bound to any theory, it is believed that the spiral configuration, particularly when used in conjunction the frustoconical members 24 induces a scraping action when the applicator member 20 is placed on the skin of the user that results in better removal of the topical substance and transfer it to the skin of the user.

In certain embodiments, it is contemplated that the tendrils 22 can be connected directly to the outer face 30 of the topical substance-conveying tube 12 in any suitable manner. In certain embodiments, tendrils such as frustoconical members 24 can be formed integral with the topical substance-conveying tube 12. Alternately it is contemplated that tendrils 22 can be connected to a sheath member 30. The sheath member 30 can be configured as a cylindrical member that can coaxially overlay the topical substance-conveying tube 12. The sheath member 30 can be maintained in contact with the outer face of the topical substance conveying tube 12 by any suitable means. Non-limiting examples of such contact or attachment means include friction fit, adhesives and the like.

The topical substance-conveying tube 12 can have any suitable inner diameter sufficient to convey topical substance there through when desired or required. In certain applications, it is contemplated that the tube 12 can have an inner diameter between 1/8 inches and 3/4 inches, with internal diameters between 1/8 and 1/2 inches in certain situations. The topical substance-conveying tube 12 will have a wall thickness sufficient to stiffen the tube 12 for use as an application device 10. In certain applications, the wall thickness of tube 12 between 1/32 and 1/8 inch.

In certain configurations, where pump dispensing is not required, the applicator device 10 can be configured with a covered cap member 31. It is contemplated that the covered cap member can be associated with a suitable telescopic wand 33 that can be movable positioned in tube 12.

In the applicator device 10 as depicted in FIG. 1, the material conveying tube 12 includes a plurality of tendrils 22 configured a plurality of frustoconical members arrayed in a circular or generally spiral configuration. As depicted in FIG. 1 the tendrils 22 can be oriented as a body projecting from the outside of the material conveying tube 12. The tendril body extends from the base 36 of the pump device 16 and extending along the material conveying tube 12 to a location distal to the pump device 16. In various embodiments, the tendril region covers between 50% and 80% of the length of the material conveying tube 12 such that the distal end of the material conveying tube projects outward from the end of the device.

The applicator device can be inserted into a suitable container device into material contained such that at least a portion of the tendrils 22 are coated with the material. The individual tendrils 22 will each container material which can be removed from the container device for application. The tendrils 22 are easily maneuverable allowing for a clean and balanced application the material. The applicator may be made of a material that is, plastic, sponge, rubber, foam, microfiber, extended foam core and/or other material(s) that allow may be coated with different substances.

Figure 9:
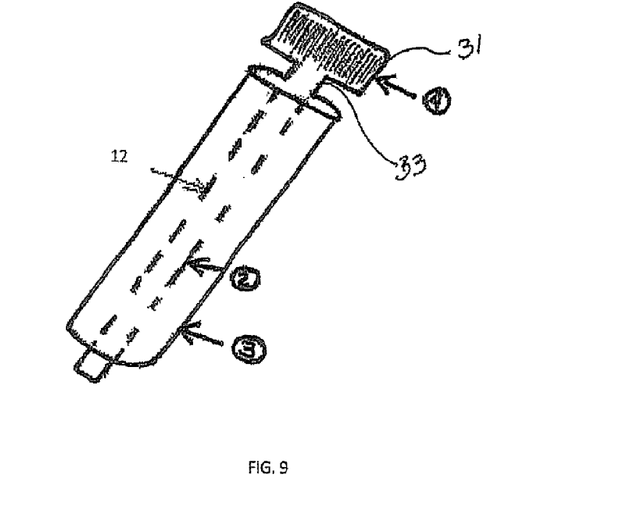
FIG. 9 is a perspective view of a fourth alternate embodiment of an applicator device as disclosed herein. perspective second embodiment of an applicator as disclosed herein.

FIG. 9 depicts an applicator device, pumps and cap device and tube that can be used to cap a bottle holding a suitable material. This applicator may be extendable and may be used in smaller bottles. There may be a rounded applicator with a larger rounded applicator casing the outside of the first applicator. The outer rounded applicator can be gently pulled down to add length to the internal applicator. The outer applicator may slide along the length of the inner applicator or an inner tube, rode or cylinder. The outer applicator may be may rotate the around the inner applicator. The slidable applicator may be useful in reaching key parts of the user's body. It may be made of a material that is, plastic, sponge, rubber, foam, microfiber, extended foam core and/or other material(s) that may be coated with different substances. The tube that may be slidable to the bottom of the applicator will have a greater diameter then the original tube.

As depicted by the illustration in FIG. 7, there is depicted a pump cap and tube inside of an example bottle of capable of holding a substance. In certain embodiments, the applicator can be configured such that the applicator material such as the tendrils can have four square edges and slants downward away from the center tube to form "flaps" or flexible wings. It may be made of a material that may be at least one of, plastic, sponge, rubber, foam, microfiber, extended foam core and/or other material(s) that may be coated with substances. At its thinnest measurement (the end of each "flap" tip) it may be rounded. The substance tube may be extended almost the length of the bottle so that the substance can still be pumped from the bottle through the tube. The tube may be hollow and may comprise any shape.

The invention has been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An applicator device comprising:
   a tube member having an elongated body with outer surface, a first end and an opposed second end;
   an applicator member attached to a portion of the outer surface of the elongated body of the tube member and extending around the circumference of the tube member, the applicator member including a plurality of flexible frustoconical tendrils projecting outward from the outer surface of the elongated member, wherein the opposed second end extends beyond the applicator member and has a fluid inlet opening;
   a cap member, the cap member connected to the tube member at a location proximate to the first end, wherein the applicator member is located distal to the cap member; and
   a pump mechanism in fluid connection with the first end of the tube member, wherein the cap is connected to the tube at a location intermediate between the applicator member and the pump mechanism.

2. The applicator device of claim 1 wherein frustoconical tendrils are oriented at an angle between 10 degrees and 90 degrees relative to the outer surface of the elongated body of the tube member.

3. The applicator device of claim 2 further comprising non-frustoconical tendrils.

4. The applicator device of claim 3 wherein the frustoconical and non-frustoconical tendrils are present in a total tendril concentration between 5 and 30 tendrils per square inch.

5. The applicator devices of claim 2 wherein the frustoconical tendrils are present in a spiral pattern.

6. The applicator device of claim 2 wherein the applicator member further comprising a sheath, the sheath overlying and contacting the outer surface of the of the elongated body of the tube member, the frustoconical tendrils integrally connected to the sheath.

7. The applicator device of claim 2 further comprising a pump mechanism in fluid connection with the first end of the tube member and a cap connected to the tube at a location intermediate between the applicator member and the pump mechanism.

8. The applicator device of claim 7 further comprising non-frustoconical tendrils.

9. The applicator device of claim 8 wherein the frustoconical and non-frustoconical tendrils are present in a total tendril concentration between 5 and 30 tendrils per square inch.

10. The applicator devices of claim 7 wherein the frustoconical tendrils are present in a spiral pattern.

11. The applicator device of claim 7 wherein the applicator member further comprising a sheath, the sheath overlying and contacting the outer surface of the of the elongated body of the tube member, the frustoconical tendrils integrally connected to the sheath.

12. An applicator and container device comprising:
    a tube member having an elongated body with outer surface, a first end and an opposed second end;
    an applicator member attached to a portion of the outer surface of the elongated body of the tube member and extending around the circumference of the tube member, the applicator member including a plurality of flexible frustoconical tendrils projecting outward from the outer surface of the elongated member, wherein the opposed second end of the tube extends beyond the applicator member and has a fluid inlet; and
    a container device, the container device having a hollow interior and an opening wherein the tube member attached applicator member are removably inserted through the opening and positioned in the hollow interior of the container.

13. The applicator and container device of claim 12 further comprising a cap member, the cap member connected to the tube member at a location proximate to the first end, the cap member releasably engageable with the opening defined in the container device.

14. The applicator and container device of claim 12 wherein frustoconical tendrils are oriented at an angle between 10 degrees and 90 degrees relative to the outer surface of the elongated body of the tube member.

15. The applicator and container device of claim 14 further comprising non-frustoconical tendrils wherein the frustoconical and non-frustoconical tendrils are present in a total tendril concentration between 5 and 30 tendrils per square inch.

16. The applicator and container device of claim 14 further comprising a pump mechanism in fluid connection with the first end of the tube member and a cap connected to the tube at a location intermediate between the applicator member and the pump mechanism.

17. The applicator and container device of claim 13 wherein the applicator member further comprising a sheath, the sheath overlying and contacting the outer surface of the of the elongated body of the tube member, the frustoconical tendrils integrally connected to the sheath.

18. An applicator comprising:
a tube member having an elongated body with outer surface, a first end and an opposed second end;
an applicator member attached to a portion of the outer surface of the elongated body of the tube member and extending around the circumference of the tube member, the applicator member including a plurality of flexible tendrils projecting outward from the outer surface of the elongated member, wherein the tendrils are present in a total tendril concentration between 5 and 30 tendrils per square inch and are oriented at an angle between 10 degrees and 90 degrees relative to the outer surface of the elongated body of the tube member, wherein the opposed second end extends beyond the applicator member and has a fluid inlet opening; and
a cap member, the cap member connected to the first end of the tube member, wherein the applicator member is located distal to the cap member.

19. The applicator device of claim 18 wherein at least a portion of the tendrils are configured as frustoconical members.

* * * * *